United States Patent
Liu et al.

(10) Patent No.: US 10,157,463 B2
(45) Date of Patent: Dec. 18, 2018

(54) METHOD AND APPARATUS FOR MEASURING AN ULTRASONIC IMAGE

(71) Applicant: General Electric Company, Schenectady, NY (US)

(72) Inventors: Gang Liu, Wuxi (CN); Shujuan An, Wuxi (CN); Yimeng Lin, Wuxi (CN); Jiajiu Yang, Wuxi (CN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/190,823

(22) Filed: Jun. 23, 2016

(65) Prior Publication Data

US 2017/0011515 A1 Jan. 12, 2017

(30) Foreign Application Priority Data

Jul. 10, 2015 (CN) .......................... 2015 1 0405642

(51) Int. Cl.

| | |
|---|---|
| *G06K 9/00* | (2006.01) |
| *A61B 8/00* | (2006.01) |
| *G06T 7/00* | (2017.01) |
| *A61B 8/08* | (2006.01) |
| *G06K 9/52* | (2006.01) |
| *G06K 9/62* | (2006.01) |
| *G06T 1/60* | (2006.01) |
| *G06T 3/40* | (2006.01) |
| *G06T 7/20* | (2017.01) |
| *G06T 11/60* | (2006.01) |

(Continued)

(52) U.S. Cl.
CPC ............ *G06T 7/0014* (2013.01); *A61B 8/465* (2013.01); *A61B 8/467* (2013.01); *A61B 8/469* (2013.01); *A61B 8/5215* (2013.01); *A61B 8/5223* (2013.01); *G06K 9/52* (2013.01); *G06K 9/6201* (2013.01); *G06T 1/60* (2013.01); *G06T 3/40* (2013.01); *G06T 7/20* (2013.01); *G06T 7/62* (2017.01); *G06T 11/60* (2013.01); *A61B 8/463* (2013.01); *G06K 2009/4666* (2013.01); *G06T 2207/10132* (2013.01); *G06T 2207/20021* (2013.01)

(58) Field of Classification Search
USPC ........ 382/100, 103, 106–107, 123, 128–134, 382/154–155, 162, 168, 173, 181, 199, 382/209, 219, 232, 254, 274–276, 382/285–298, 305, 312; 600/437, 443; 351/212
See application file for complete search history.

(56) References Cited

U.S. PATENT DOCUMENTS

| | | | |
|---|---|---|---|
| 5,795,296 A | 8/1998 | Pathak et al. | |
| 7,219,997 B2 * | 5/2007 | Yokota | A61B 3/12 351/212 |
| 8,144,961 B2 | 3/2012 | Lee et al. | |

(Continued)

FOREIGN PATENT DOCUMENTS

| | | |
|---|---|---|
| EP | 2302587 A1 | 3/2011 |
| JP | 2016158679 A | 9/2016 |

*Primary Examiner* — Seyed Azarian

(57) ABSTRACT

The present invention relates to a method and apparatus for measuring an ultrasonic image. The method comprises: a measuring template loading step: loading a measuring template according to a received instruction; and a measuring template displaying step: displaying a selected measuring template at a designated position on the ultrasonic image.

10 Claims, 4 Drawing Sheets

(51) Int. Cl.
*G06T 7/62* (2017.01)
*G06K 9/46* (2006.01)

(56) References Cited

U.S. PATENT DOCUMENTS

| | | | | |
|---|---|---|---|---|
| 8,888,704 | B2 | 11/2014 | Imamura et al. | |
| 2009/0198133 | A1* | 8/2009 | Kawagishi | A61B 8/08 600/443 |
| 2010/0074475 | A1* | 3/2010 | Chouno | A61B 5/055 382/107 |
| 2010/0210946 | A1* | 8/2010 | Harada | A61B 5/489 600/443 |
| 2011/0282199 | A1* | 11/2011 | Lee | A61B 5/1075 600/437 |
| 2014/0005530 | A1 | 1/2014 | Liu et al. | |
| 2016/0249884 | A1 | 9/2016 | Hashimoto et al. | |

\* cited by examiner

PROPERTIES OF THE MEASURING TEMPLATE

| | |
|---|---|
| NAME: | MEASURING TEMPLATE FOR AN IVC |
| LENGTH: | 2.1CM |
| COLOR OF A MIDPOINT: | RED |
| ROTATABLE ANGLE: | 0-180 |

PROPERTIES OF THE MEASURING TEMPLATE

| | |
|---|---|
| NAME: | MEASURING TEMPLATE FOR A LEFT VENTRICULAR SYSTOLIC |
| DIAMETER OF AN INNER CIRCLE: | 3.0cm |
| DIAMETER OF AN OUTER CIRCLE: | 4.5cm |
| NUMBER OF CIRCLES: | 2 |

METHOD AND APPARATUS FOR MEASURING AN ULTRASONIC IMAGE

CROSS-REFERENCE TO RELATED APPLICATIONS

This application claims priority to Chinese patent application serial number 201510405642.4, filed on Jul. 10, 2015, the entirety of which is incorporated herein by reference.

BACKGROUND

When an ultrasound machine is used clinically, usually some positions on an ultrasonic image in which a doctor is interested need to be measured. For example, a length, a thickness, a width, an area, an angle and the like of some organs/tissues on the ultrasonic image are measured.

During ultrasonic scanning, the obtained ultrasonic image will change continuously. Such ultrasonic image that is changing continuously over time is referred to as a live ultrasonic image. In the existing method for measuring an ultrasonic image, usually, the live ultrasonic image will firstly be frozen to obtain a still ultrasonic image, and then a position of interest on the still ultrasonic image is measured by a user's manual operation or by an image automatic recognition.

However, in some clinical application scenarios, a general pathological change for a patient needs to be diagnosed quickly from an ultrasonic image to obtain a qualitative conclusion. An accurate measurement is not necessary. For example, when pathological condition is positioned on an emergency patient in an ultrasonic manner at an emergency department, since time is running out, a focus needs to be found quickly and a preliminary conclusion needs to be obtained. Moreover, in a hospital with a huge amount of ultrasonic scanning, some objects to be scanned may only need a preliminary qualitative conclusion, and thus an accurate measurement is not necessary.

In the above application scenarios, it takes too much time to obtain unnecessary measurements in the existing method for measuring the ultrasonic image.

BRIEF SUMMARY OF INVENTION

In an embodiment, a method for measuring an ultrasonic image, comprising: a measuring template loading step: loading a measuring template according to a received instruction; and a measuring template displaying step: displaying a selected measuring template at a designated position on the ultrasonic image.

In an embodiment, an apparatus for measuring an ultrasonic image, comprising: a measuring template loading module for loading a measuring template according to a received instruction; and a measuring template displaying module for displaying a selected measuring template at a designated position on the ultrasonic image.

BRIEF DESCRIPTION OF THE DRAWINGS

The present invention can be better understood in light of the following description of embodiments of the present invention with reference to the accompanying drawings, in which.

DETAILED DESCRIPTION OF THE DRAWINGS

Figure 1:
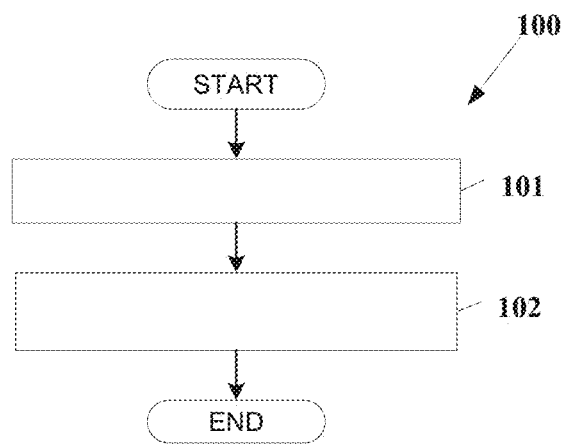
FIG. 1 is a schematic flow chart of one embodiment of a method for measuring an ultrasonic image according to the present invention.

Hereafter, a detailed description will be given for preferred embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art relating to the contents disclosed in the present invention, which should not be regarded as insufficient disclosure of the present invention.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present utility model do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

In order to make the purpose, the technical solutions and the advantages of the invention more apparent, the technical solutions of the present invention will be set forth clearly and fully in the following by combining with specific embodiments of the invention and the corresponding accompanying drawings. Obviously, the described embodiments are merely part—not all—of the embodiments in the present invention. In view of the embodiments in the present invention, other embodiments made by one of ordinary skilled in the art without inventive work all fall within the scope of protection of the invention.

According to an embodiment of the present invention, a method for measuring an ultrasonic image is provided. In one embodiment of the present invention, the method may be used for measuring a live ultrasonic image. The following description is for measuring the live ultrasonic image. Of course, the method may also be used for measuring a still ultrasonic image.

With reference to FIG. 1, FIG. 1 illustrates a schematic flow chart of one embodiment 100 of a method for measuring an ultrasonic image according to the present invention. The embodiment 100 may comprise the following Steps 101-102.

As shown in FIG. 1, Step 101 is a measuring template loading step: loading a measuring template according to a received instruction.

Specifically, after a corresponding instruction is received, a pre-generated measuring template may be loaded and displayed for selection by the user.

In one embodiment of the present invention, the instruction may be triggered by the user or may be automatically triggered by a computer program.

Figure 2:
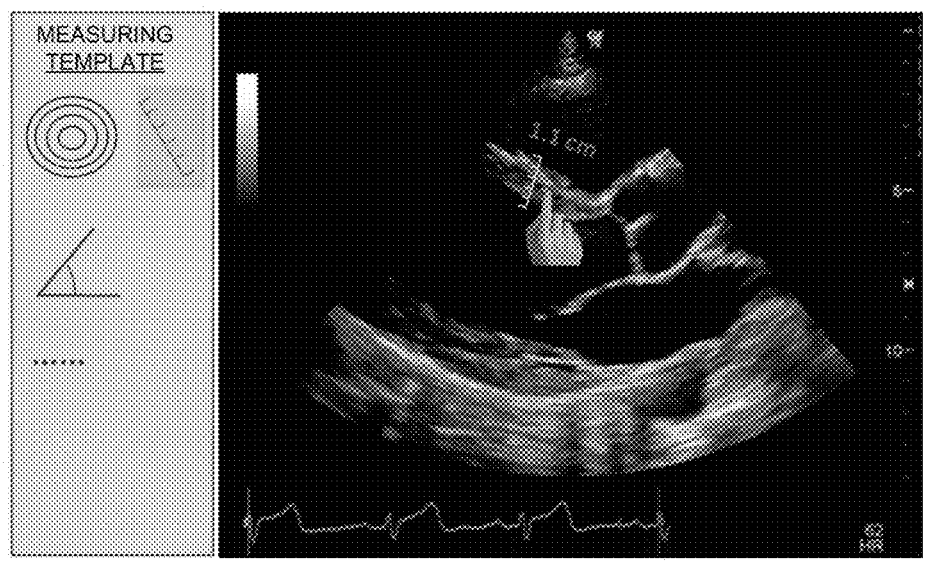
FIG. 2 is a schematic diagram of one embodiment of information present on an ultrasound machine when an ultrasonic image is measured by the method as shown in FIG. 1.

In the clinical application environments, when an organ or tissue to be measured needs to be measured quickly, the measuring template may be loaded by the instruction triggered by the user or the instruction automatically triggered by the program, and the measuring template may be displayed for selection by the user. With reference to FIG. 2, the left half of FIG. 2 is one embodiment of a measuring template displayed on an ultrasound machine for selection by the user after Step 101 is performed. Although only three measuring templates are shown in FIG. 2, those skilled in the art should recognize that the number and types of the measuring templates needing to be loaded may be decided by the user himself or automatically selected for the user by the program.

Step 102 is a measuring template displaying step: displaying a selected measuring template at a designated position on the ultrasonic image.

Specifically, when the user selects a certain measuring template, the measuring template may be displayed at a position designated by the user on the ultrasonic image.

In the clinical application environments, when a certain loaded measuring template is selected by the user by ways of touching, mouse or keyboard control, etc., said measuring template may be placed and displayed at a proper position determined by the user on the live ultrasonic image by way of being dragged or being clicked, etc. With reference to FIG. 2, the right half of FIG. 2 is one measuring template displayed on a live ultrasonic image after Step 102 is performed. For convenience of observation, the color of the measuring template on the live ultrasonic image may be obviously distinct from the color of the live ultrasonic image itself.

Figure 3:
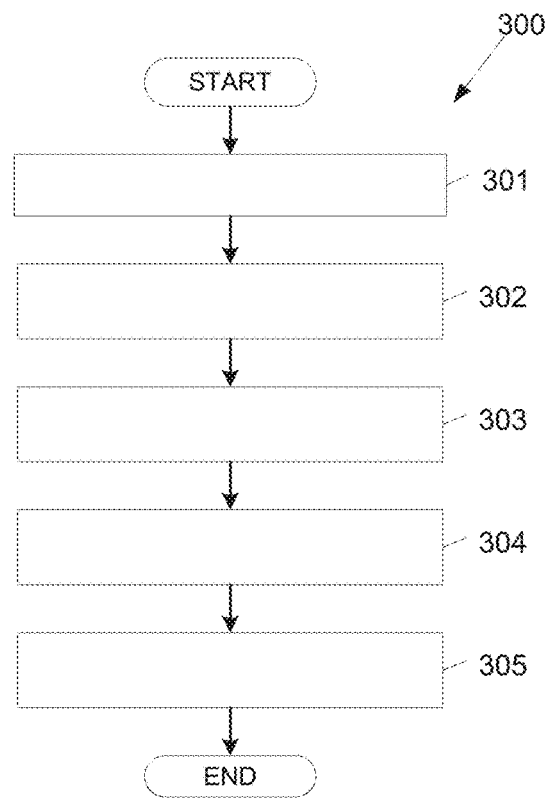
FIG. 3 is a schematic flow chart of another embodiment of the method for measuring the ultrasonic image according to the present invention.

With reference to FIG. 3, FIG. 3 is a schematic flow chart of another embodiment 300 of the method for measuring the ultrasonic image according to the present invention. The embodiment 300 may comprise Steps 301-305. Specifically, Step 302 is similar to the above Step 101, which will not be repetitively described herein. Specifically, Step 303 is similar to the above Step 102, which will not be repetitively described herein either.

Step 301 is a measuring template generating step: generating a measuring template according to clinical experience data of a measured object on the ultrasonic image where the measuring template is applied and storing the measuring template.

In order to complete the measuring more quickly during clinical application, the measuring template may be generated and stored by a manufacturer or a user in advance.

In one embodiment of the present invention, some parameters which are needed at the time of generating the measuring template may be obtained according to the clinical experience data of the measured object on the ultrasonic image.

Generating a length measuring template and generating an area measuring template are taken as an example respectively in the following, to explain a measuring template generating process. Other types of measuring templates (e.g., an angle measuring template) may also be generated by a similar method.

Figure 4:
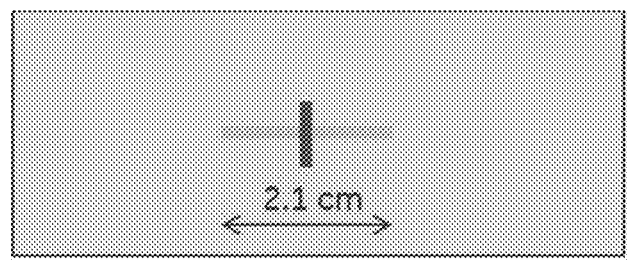
FIG. 4 is a schematic diagram of one embodiment of generating a length measuring template in a measuring template generating step in the method as shown in FIG. 3.

The length measuring template may be used for measuring a length or thickness of a certain organ or tissue on the ultrasonic image. A length of the length measuring template is a key parameter thereof, which may be determined according to the clinical experience data of the measured object. For example, clinically, an inferior vena cava (IVC) collapse rate and a right atrium pressure of a patient may be calculated by measuring a diameter of an IVC on the ultrasonic image. According to the clinical experience data, when the diameter of the IVC exceeds 2.1 cm and the IVC collapse rate is less than 50%, the right atrium pressure is generally at 15 mmHg; when the diameter of the IVC is less than 2.1 cm and the IVC collapse rate is less than 50%, the right atrium pressure is at 5-10 mmHg; and when the diameter of the IVC is equal to 2.1 cm and the IVC collapse rate is greater than 50%, the right atrium pressure is generally at 3 mmHg. It can be seen that 2.1 cm is one important critical value of the diameter of the IVC. Therefore, with reference to FIG. 4, when the length measuring template for measuring the diameter of the IVC is generated, the shape of the template may be configured to be straight-line segments whose length may be 2.1 cm. Moreover, information such as a name of the template, a color of a midpoint (red in FIG. 4), an angle range in which the user is allowed to rotate the template, etc. may also be inputted.

Figure 5:
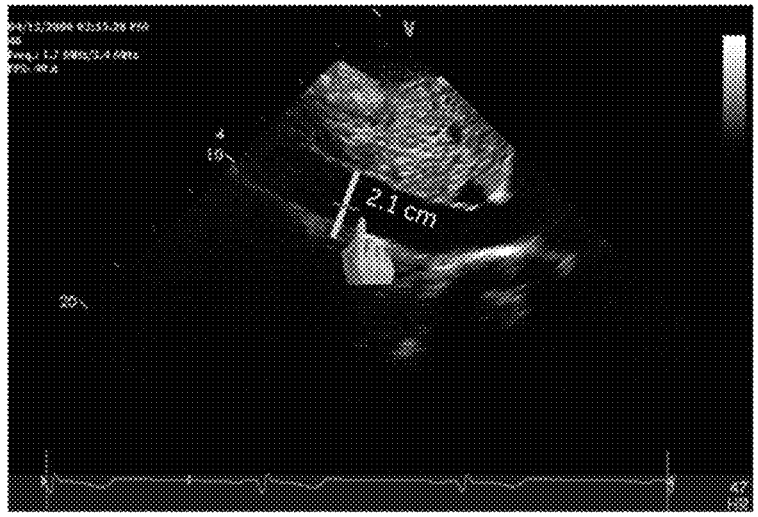
FIG. 5 illustrates a schematic diagram of one embodiment of measuring the ultrasonic image by applying the length measuring template there onto.

With reference to FIG. 5, after the user has selected the above length measuring template for measuring the diameter of the IVC, a qualitative conclusion whether the diameter of the IVC on the image exceeds 2.1 cm may be obtained easily only by placing the template at a proper position on the live ultrasonic image by way of dragging or clicking, etc. (indicated by a hand in FIG. 5), instead of firstly freezing the ultrasonic image and then performing measuring.

In one embodiment of the present invention, multiple length measuring templates may be generated for different objects to be measured. For example, it is generally believed clinically that a thickness of normal left and right ventricular septum should be about 1.1 cm, and thus a length measuring template with a length of 1.1 cm for measuring the thickness of the left and right ventricular septum may be generated. When the user needs to measure the thickness of the left and right ventricular septum, as shown in the right half of FIG. 2, only by selecting the template and placing the template at a proper position on the live ultrasonic image, it can just be seen quickly whether the thickness of the left and right ventricular septum is greater than 1.1 cm or less than 1.1 cm.

Figure 6:
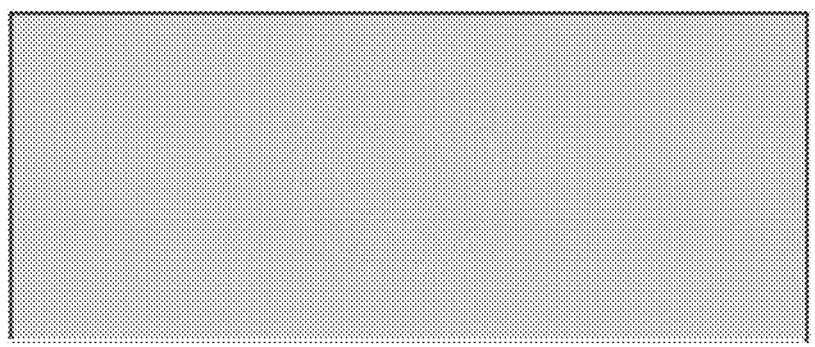
FIG. 6 is a schematic diagram of one embodiment of generating an area measuring template in the measuring template generating step in the method as shown in FIG. 3.

The area measuring template may be used for measuring an area of a certain organ or tissue on the ultrasonic image. The area measuring template may be a circle, an ellipse or any enclosed plane figure. An area of the area measuring template is one key parameter thereof. When the area measuring template is circle, its diameter decides its area, and the diameter may be determined according to the clinical experience data of the measured object. For example, it may be estimated clinically whether a systolic function of the left ventricular is normal or not by measuring systolic and diastolic areas of the left ventricular. In normal conditions, when the left ventricular is systolic, a diameter of its corresponding region is no less than 3 cm, and when the left ventricular is diastolic, a diameter of its corresponding region is no more than 4.5 cm. It can be seen that 3 cm and 4.5 cm are key clinical data for qualitatively deciding whether the systolic function of the left ventricular is normal or not. Thus, with reference to FIG. 6, when the measuring template for estimating the systolic function of the left ventricular is generated, the shape of the template may be configured to be two concentric circles, in which a diameter of the inner circle may be 3 cm and a diameter of the outer circle may be 4.5 cm. Moreover, information such as the name of the template may also be inputted.

Figure 7:
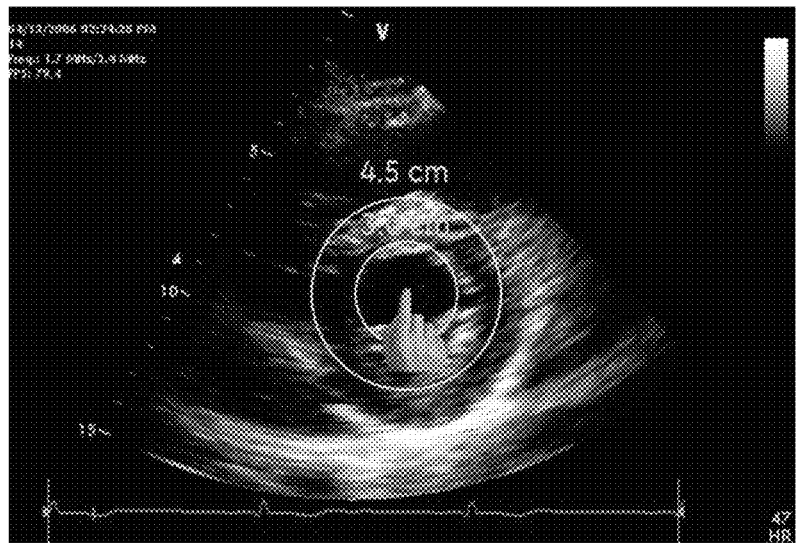
FIG. 7 is a schematic diagram of one embodiment of measuring the ultrasonic image by applying the area measuring template there onto.

With reference to FIG. 7, after the user has selected the above area measuring template for estimating the systolic function of the left ventricular, only by placing the template at a proper position on the live ultrasonic image by way of dragging or clicking, etc. (indicated by a hand in FIG. 7), a qualitative conclusion whether the diameter range of the left ventricular when being systolic and diastolic on the image is between 3 cm and 4.5 cm or not can just be obtained quickly, instead of firstly freezing the ultrasonic image and then performing measuring.

In one embodiment of the present invention, multiple area measuring templates may also be generated for different measured objects.

Step 304 is a measuring template moving step: shifting and/or rotating the measuring template on the ultrasonic image according to the received instruction.

In one embodiment of the present invention, after the selected measuring template is displayed on the ultrasonic image, the measuring template may be shifted and/or rotated on the ultrasonic image according to the received instruction (e.g., by way of mouse click, keyboard control, touch control, etc.). In this way, the measuring template can just be moved to a proper position.

Step 305 is a measuring-template-size adjusting step: adjusting a size of the measuring template on the ultrasonic image according to the received instruction.

In one embodiment of the present invention, after the selected measuring template is displayed on the ultrasonic image, the size of the measuring template itself may be changed according to the received instruction (e.g., by way of mouse click, keyboard control, touch control, etc.). For example, the length of the length measuring template, the area and/or shape of the area measuring template, the angle of the angle measuring template and the like may be changed.

So far, the method for measuring the ultrasonic image according to the embodiments of the present invention has been described. According to the method of the present invention, measuring can be completed directly and quickly on the live ultrasonic image and the preliminary conclusion can be obtained. Similar to the method, the present invention also provides the corresponding apparatus.

Figure 8:
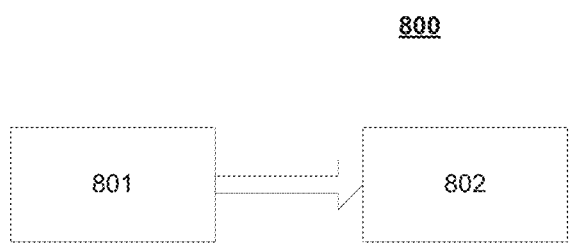
FIG. 8 is a schematic block diagram of one embodiment of an apparatus for measuring an ultrasonic image according to the present invention.

FIG. 8 illustrates a schematic block diagram of one embodiment of an apparatus for measuring an ultrasonic image according to the present invention.

As shown in FIG. 8, the apparatus 800 may include: a measuring template loading module 801 for loading a measuring template according to a received instruction; a measuring template displaying module 802 for displaying a selected measuring template at a designated position on the ultrasonic image.

In one embodiment of the present invention, the ultrasonic image is a live ultrasonic image.

In one embodiment of the present invention, the apparatus 800 may also include a measuring template generating module for generating the measuring template according to clinical experience data of a measured object on the ultrasonic image where the measuring template is applied and storing the measuring template.

In one embodiment of the present invention, the measuring template generating module may further include: a module for generating a length measuring template according to the clinical experience data; a module for generating an area measuring template according to the clinical experience data; and a module for generating an angle measuring template according to the clinical experience data.

In one embodiment of the present invention, the length measuring template includes straight-line segments which contain length information and midpoint position information.

In one embodiment of the present invention, the area measuring template contains an enclosed plane figure.

In one embodiment of the present invention, the area measuring template contains at least one circle.

In one embodiment of the present invention, the area measuring template contains multiple concentric circles.

In one embodiment of the present invention, the apparatus 800 may also include a measuring template moving module for shifting and/or rotating the measuring template on the ultrasonic image according to the received instruction.

In one embodiment of the present invention, the apparatus 800 may also include a measuring-template-size adjusting module for adjusting a size of the measuring template on the ultrasonic image according to the received instruction.

So far, the apparatus for measuring the ultrasonic image according to the embodiments of the present invention has been described. Similar to the above method, according to the apparatus of the present invention, measuring can be completed directly and quickly on the live ultrasonic image and the preliminary conclusion can be obtained.

The above descriptions are merely embodiments of the invention and are not intended to restrict the scope of the invention. All kinds of variations and modifications could be made to the present invention to those skilled in the art. Any modifications, alternatives and improvements made within the spirit and principles of the present invention shall fall within the scope of the appended claims.

We claim:

1. A method for measuring an object in a live ultrasonic image, comprising:
   generating a plurality of measuring templates, wherein generating the plurality of measuring templates comprises:
   generating a length measuring template according to clinical experience data;
   generating an area measuring template according to said clinical experience data; and generating an angle measuring template according to said clinical experience data;

displaying the plurality of measuring templates;

selecting one of the plurality of measuring templates;

loading the one of the plurality of measuring templates according to a first received instruction from a user;

receiving the live ultrasonic image generated from an ultrasonic diagnostic apparatus;

displaying the one of the plurality of measuring templates on the live ultrasonic image;

adjusting a size of the one of the plurality of measuring templates based on a second received instruction from the user;

moving the one of the plurality of measuring templates to a proper position with respect to the object in the live ultrasonic image by rotating or shifting the one of the plurality of measuring templates based on a third received instruction from the user; and qualitatively comparing the live ultrasonic image to the one of the plurality of measuring templates to obtain a qualitative conclusion about the object with respect to the one of the plurality of measuring templates.

2. The method according to claim 1, wherein said length measuring template contains straight-line segments which contain length information and midpoint position information.

3. The method according to claim 1, wherein said area measuring template contains an enclosed plane figure.

4. The method according to claim 1, wherein said area measuring template contains at least one circle.

5. The method according to claim 1, wherein said area measuring template contains a plurality of concentric circles.

6. An ultrasound machine for measuring a live ultrasonic image, comprising:

an ultrasonic probe for transmitting ultrasonic pulses used by the ultrasound machine to generate the live ultrasonic image;

a measuring template generating module for generating a plurality of measuring templates, where each of the plurality of measuring templates is generated according to clinical experience data, wherein said measuring template generating module further comprises:

a module for generating a length measuring template according to said clinical experience data, wherein said length measuring template contains straight-line segments which contain length information and midpoint position information;

a module for generating an area measuring template according to said clinical experience data; and a module for generating an angle measuring template according to said clinical experience data a measuring template loading module for loading one of the plurality of measuring templates according to a first received instruction from a user, where the first received instruction comprises the selection of the one of the plurality of measuring templates; and a measuring template displaying module for displaying the one of the plurality of measuring templates at a designated position on said live ultrasonic image:

a measuring template moving module for shifting or rotating the one of the plurality of measuring templates on the live ultrasonic image according to a second received instruction from the user so that the user can position the one of the plurality of measuring templates at a proper position on the live ultrasonic image to obtain a qualitative measurement of an object in the live ultrasonic image using the one of the plurality of measuring templates.

7. The ultrasound machine according to claim 6, wherein said area measuring template contains an enclosed plane figure.

8. The ultrasound machine according to claim 6, wherein said area measuring template contains at least one circle.

9. The ultrasound machine according to claim 6, wherein said area measuring template contains a plurality of concentric circles.

10. The ultrasound machine according to claim 6, further comprising:

a measuring-template-size adjusting module for adjusting a size of said one of the plurality of measuring templates on said ultrasonic image according to a third received instruction from the user.

* * * * *